United States Patent [19]

Cowan

[11] Patent Number: 5,334,201
[45] Date of Patent: Aug. 2, 1994

[54] PERMANENT STENT MADE OF A CROSS LINKABLE MATERIAL

[76] Inventor: Kevin P. Cowan, 4242 Estates Ct., Allison Park, Pa. 15101

[21] Appl. No.: 30,977

[22] Filed: Mar. 12, 1993

[51] Int. Cl.⁵ .............................................. A61F 2/06
[52] U.S. Cl. .................................... 623/1; 606/194
[58] Field of Search ............... 623/1, 66; 600/36; 606/194

[56] References Cited

U.S. PATENT DOCUMENTS

| | | | |
|---|---|---|---|
| 3,562,352 | 2/1971 | Nyilas | 623/1 |
| 3,808,113 | 4/1974 | Okamura et al. | 623/1 |
| 4,132,746 | 1/1979 | Urry et al. | 623/1 |
| 4,135,494 | 1/1979 | Stoner et al. | 623/1 |
| 4,183,102 | 1/1980 | Guiset | 623/1 |
| 4,202,349 | 5/1980 | Jones | 623/1 |
| 4,304,010 | 12/1981 | Mano | 623/1 |
| 4,377,010 | 3/1983 | Fydelor et al. | 623/1 |
| 4,676,975 | 6/1987 | McGary et al. | 623/1 |
| 4,731,073 | 3/1988 | Robinson | 623/1 |
| 4,798,607 | 1/1989 | Middleton et al. | 623/1 |
| 4,904,272 | 2/1990 | Middleton et al. | 623/1 |
| 4,906,465 | 3/1990 | Chaikof et al. | 623/1 |
| 4,955,899 | 9/1990 | Della Corna et al. | 623/1 |
| 4,979,959 | 12/1990 | Guire | 623/1 |
| 5,019,096 | 5/1991 | Fox, Jr. et al. | 623/1 |
| 5,024,232 | 6/1991 | Smid et al. | 623/1 |
| 5,059,211 | 10/1991 | Stack et al. | 606/108 |
| 5,064,435 | 11/1991 | Porter | 623/12 |
| 5,100,429 | 3/1992 | Sinofsky et al. | 606/195 |
| 5,100,689 | 3/1992 | Goldberg et al. | 623/1 |
| 5,152,782 | 10/1992 | Kowligi et al. | 623/1 |
| 5,152,783 | 10/1992 | Suzuki et al. | 623/1 |
| 5,192,308 | 3/1993 | Ostapchenko | 623/1 |
| 5,192,310 | 3/1993 | Herweck et al. | 623/1 |
| 5,207,706 | 5/1993 | Manaker | 623/1 |
| 5,211,658 | 5/1993 | Clouse | 623/1 |

*Primary Examiner*—Randy C. Shay
*Attorney, Agent, or Firm*—Keck, Mahin & Cate

[57] ABSTRACT

An improved vascular reinforcing stent for use in angioplasty which comprises a sleeve tubular stent of a cross-linkable substance that is completely encapsulated within a biologically compatible film and a process for using such a stent.

10 Claims, 1 Drawing Sheet

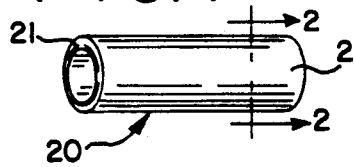
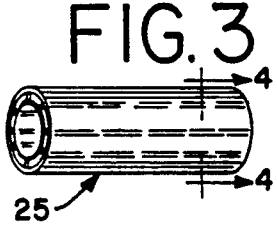
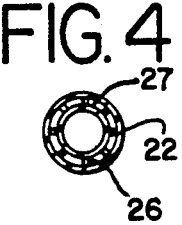
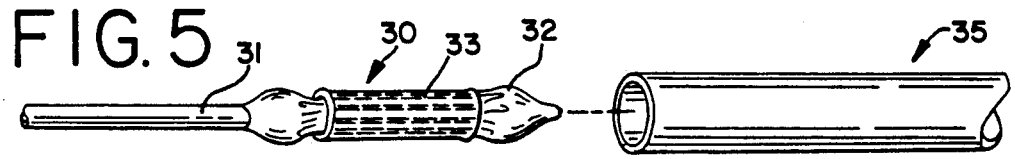
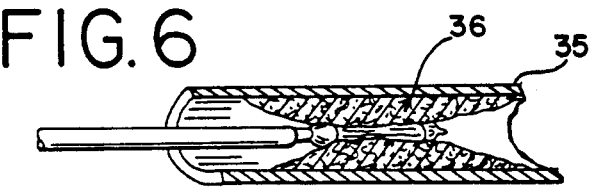
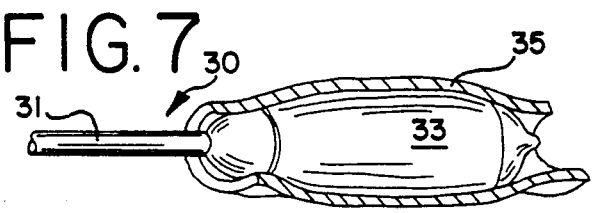
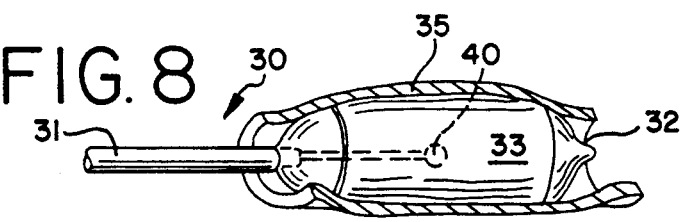
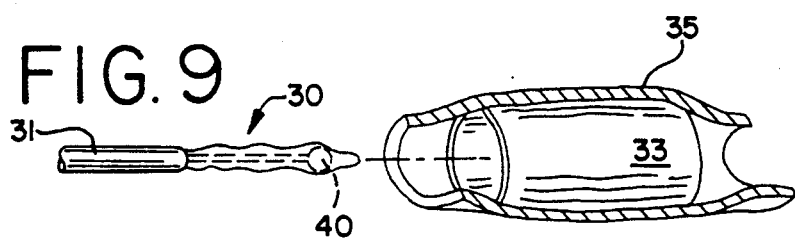

PERMANENT STENT MADE OF A CROSS LINKABLE MATERIAL

FIELD OF THE INVENTION

This invention relates to an endovascular stent for use in reducing restinosis in a blood vessel after dilation by balloon angioplasty and more particularly to an endovascular stent sleeve having an expansible tubular body portion composed of a cross-linkable or curable substance and having a biologically compatible encapsulating film which completely surrounds the tubular body portion to isolate it from the blood vessel into which it is intraluminally inserted.

BACKGROUND OF THE INVENTION

Angioplasty, and especially balloon angioplasty, has become an accepted and widely used procedure for dilating stenotic regions of blood vessels, such as, for example, coronary arteries. Dilation of the stenosed region by inflation of a balloon or some other type of angioplasty is usually effective in increasing the diameter of the vessel lumen so that circulation is increased. However, for reasons that are not clearly understood the situation occurs frequently that the dilated, stenosed region undergoes restenosis, with concomitant re-impairment of blood circulation.

One procedure that has been proposed to mitigate the problem of restenosis is that of intraluminal insertion of an endovascular stent into the stenosed region of a blood vessel by means of a catheter.

In balloon angioplasty the stent is placed around the balloon head of a balloon catheter while in non-expanded condition and the catheter, with the stent and the balloon, is inserted into the area of the stenosis, at which time the balloon is inflated to increase the diameter of the stent and simultaneously dilate the stenosed vascular region. After the stent has been enlarged in diameter and forced outwardly against the wall of the blood vessel, the balloon is deflated and it, together with the catheter to which it is attached, is removed from the patient. In the past, a number of different stent configurations have been proposed for coping with the problem of restenosis. For example, a variety of springs constructed of materials possessing shape-memory have been suggested for use. In this application, the spring is of a relatively small diameter initially but when heated to an appropriate temperature, the material from which the spring is made remembers its original shape and expands to a larger diameter, thus exerting pressure against the vessel wall. In other instances, woven metal stents have been suggested in which the rigidity or hoop strength of the material itself is great enough to sustain pressure outwardly against the wall of the vessel into which it has been placed. For example, in U.S. Pat. No. 5,059,211, there is proposed an absorbable vascular stent in which a sheet of material is formed into a cylinder with the ends overlapping so that it can be enlarged from a relatively small to a relatively larger diameter after insertion into the body.

In U.S. Pat. No. 5,064,435, there is disclosed an implantable stent made up of two or more generally tubular coaxially and slidably connected segments, each of the segments being made of multiple braided helically wound strands of resilient material.

U.S. Pat. No. 5,100,429 teaches a stent which is comprised of a sheet of flexible biologically compatible material that is rolled so that the ends of the sheet overlap to form a generally tubular body. This tubular body is wrapped around the balloon head of a catheter and intraluminally inserted into position at which time it is subjected to ultra violet light which then causes the overlapped regions of the sheet to cross-link and bond the ends of the sheet together. Such a sheet is non-stretchable and can fold on itself, facts which may result in non-bonding of the ends in the required manner. Thus, the diameter of the stent is formed after it has been dilated to the required diameter and then cured to set the final diameter that is to be used. This patent also suggests the possibility of surrounding the balloon head with a collagen-based material and then inserting the apparatus into the blood vessel. After the collagen-based material has been inserted into the required position and enlarged, it is subjected to laser or other energy source to effect complete curing of the material so that it remains in its final size and position in the artery. A difficulty with this arrangement is the fact that the cross-linkable or curable materials used are toxic in their raw or uncured state and thus, constitute a health hazard.

DESCRIPTION OF THE DRAWINGS

It is a principal object of this invention to provide an endovascular stent that utilizes a cross-linkable substance that is encapsulated within a biologically compatible protective film.

Another object of this invention is to provide an endovascular stent that can be transluminally inserted into position in an uncured state and then cured, without the material of the uncured stent becoming exposed to the surrounding vessel.

A further object of this invention is to provide an endovascular stent that is encapsulated in a biologically compatible film that separates the tubular support body of the stent from the blood vessel into which it is to be inserted.

Still a further object of this invention is to provide an endovascular stent that is encapsulated in a film that is impregnated with an antithrombogenic agent.

Yet another object of this invention is to provide a process for treating a stenosed region of a blood vessel.

Still another object of this invention is to provide a system for utilizing an endovascular stent that is initially in an uncured condition.

Other objects and advantages of this invention will be in part obvious and in part explained by reference to the accompanying specification and drawings, in which:

FIG. 1 is a side view of a sleeve stent having a encapsulated tubular body in accordance with this invention;

FIG. 2 is a section taken along the line 2—2 of FIG. 1.

FIG. 3 is a side view of a modified form of stent;

FIG. 4 is a cross-section view taken along the line 4—4 of FIG. 3;

FIG. 5 is a an exploded view showing the manner in which the stent is placed about the balloon head of the catheter for insertion into a blood vessel;

FIG. 6 is a view showing how the unexpanded stent is located in the stenotic region of a blood vessel;

FIG. 7 is a view showing how the stent has been dilated by expansion of the balloon to enlarge the diameter of the stenosed area;

FIG. 8 is a view similar to FIG. 7 but showing the positioning of a light source used to effect curing of the cross-linkable material that forms a part of the stent; and FIG. 9 is a view showing the stent in position in its fully cured condition and illustrating the manner of withdrawal of the balloon catheter.

SUMMARY OF THE INVENTION

As indicated earlier, the present invention involves the use of a cross-linkable or curable substance for the manufacture of a medical stent, which substance can be cured by exposure to radiation, such as laser or ultraviolet light or heat. The substance when in the uncured condition is normally toxic and as such represents a health hazard but, after it has been cured, it is completely non-toxic. The curing of the material at the site of the stenosis permits the stent sleeve to be of a small diameter when initially inserted intraluminally into the body and then expanded by appropriate angioplasty means to a final, larger diameter. The stent sleeve has a radially expansible tubular body portion which as noted above is formed in part of a cross-linkable substance that can be cured to a final hardness which will provide sufficient hoop strength to resist restenosis of the vessel wall or to repair an aneurysm in the vessel. The body portion may be partially cured prior to insertion into the blood vessel or may be inserted in the completely non-cured condition. In either instance, the cross-linkable material is toxic and must be isolated from the surrounding membrane. Since most of the materials presently known which are cross-linkable and can be used in the present device are also toxic to the body, the present invention contemplates the use of an encapsulating film that completely surrounds the stent sleeve to isolate it from the blood vessel into which it has been inserted. The encapsulating medium must be biologically compatible with the vessel itself and must also remain completely integral during the process of enlarging the stent to its final implanted diameter.

To understand the present invention more fully, reference is made to the drawings and first to FIGS. 1 and 2. FIG. 1 shows a generally side elevation of a endovascular stent constructed in accordance with this invention. The stent 20 is used for resisting restinosis in a stenosed region of a blood vessel that has been expanded by angioplasty. The stent sleeve 20 comprises a radially expansible tubular body portion 21 (see FIG. 2) which is composed of a cross-linkable substance which can be cured by exposure to radiation or other suitable curing agents. It is significant that the stent body expand in the radial direction only and that it not increase in length. To this end, it is possible to incorporate thin, strips of a noble metal into body portion 21 to prevent longitudinal stretch. Metals such as stainless steel, silver, gold or platinum could be used and these will have the beneficial effect of making the body 21 visible to X-rays. Curable substances include epoxies, urethanes, etc. which can be cross-linked by exposure to U.V. light radiation. Polyurethane oligomer mixtures have been used and found to have desireable physical properties for permanent implantation. An example of one such urethane contained 20-30% N-Vinyl-2-Pyrrolidone, 3-6% high boiling (meth) acrylate, 1-3% photoiniator; 1-2% organosilane and 65-75% urethane oligomer.

Depending upon the particular cross-linkable substance that is chosen, the type and duration of radiation that is utilized can be adjusted in accord with known procedures. For example, radiation with energy of various wavelengths such as visible light, ultra-violet light or by use of laser are all possibilities. Similarly, radiation can be done by the application of heat or in some instances, possibly even by means of chemical reactant. The easiest forms of energy to use are, of course, light radiation since they lend themselves to relatively easy insertion into the interior of the stent so that it can be uniformly subjected to the curing radiation.

Fiber optic, gas or liquid filled tubing/bundle can be used to transmit light from source to light emitting tip which is passed, inside the catheter. Referring again to FIG. 2, it will be seen that the expansible tubular body portion 21 is completely encapsulated within a film of material 22. The material that is used to encapsulate the tubular body portion 21 must be biologically compatible with the blood vessel within which the stent is to be located. FIG. 2 clearly illustrates that the film 22 surrounds all of the external surfaces of the curable substance of expansible body portion 21. It has been found that suitable material which is biologically compatible with body tissue is a medical grade of silicone or other stretchable biologically compatible materials. Such a silicone material is elastic and will remain integral during enlargement of the stent sleeve during dilation of the stenosed region of the blood vessel.

Referring to FIGS. 3 and 4 of the drawings, there is shown a slightly modified configuration of the stent illustrated in FIGS. 1 and 2. In this case, the tubular body portion 25 is constructed with a plurality of outwardly extending protrusions 26 that create a plurality of individual chambers 27 to thereby insure an even flow of the material to be hardened. Still present, of course, is the film 22 which completely covers both the inner and outer surface of the tubular body portion 25. The protrusions 26 may incorporate the strips of nobel metal in the body portions 21, if desired, to provide resistance against longitudinal stretching, as mentioned above. These strips may be bent 90° so that the tabs protrude radially outside the sleeve and offer another means of securing the stent in place after inflation curing.

FIG. 5 shows a catheter assembly 30 which is comprised of a catheter tube 31 to which is attached a balloon head 32. Mounted around or positioned on the balloon head 32 is the tubular stent 33 which is in a non-expanded form that is of a diameter smaller than the inner diameter of the blood vessel 35 into which it is to be inserted.

After the catheter 30 is inserted into the lumen of vessel 35, the balloon end with the tubular stent 33 is moved into the stenosed region of the blood vessel 35, as shown in FIG. 6. The numeral 36 identifies the buildup of plaque material that restricts the internal diameter of vessel 35. In order to dilate the stenosed region, after the balloon and stent are located at the stenosed region, the balloon is then enlarged as shown in FIG. 7 so that the stent 33 moves outwardly towards the wall of vessel 35 and increases the internal diameter of vessel 35. While in the inflated or expanded condition, a suitable light source as indicated by numeral 40 in FIG. 8 is moved into the interior of the balloon head 32 and the sleeve is irradiated to effect curing of the sleeve material.

After initial irradiation, some shadow curing may result until the curing operation is finally complete.

Finally in FIG. 9, the stent sleeve 33 is shown completely cured and is of sufficient strength to maintain the vessel wall 35 in its dilated condition thereby mitigating the previously existing restriction to the flow of blood that was occasioned by the buildup of plaque 36. At this time, the catheter 30 is removed after the balloon head 32 is deflated and the catheter is removed from the patient's body. At this time, the stent is held in place by the elasticity of the vessel.

Thus, the overall method of treating a stenosed region of the blood vessel comprises first providing an expansible stent which has a tubular body portion composed of a cross-linkable substance the cures upon exposure to radiation and secondly, a film of a biologically compatible material that encapsulates the cross-linkable substance to isolate it from contact with the patient's tissue. The stent is placed over the balloon of a balloon catheter devices and the combination then inserted into the blood vessel and the balloon head and overlying stent positioned at the stenosed region. Following positioning in this fashion, the balloon is inflated to expand the stent to a preselected diameter after which radiation is used to effect curing of the cross-linkable substance. Finally, the balloon is deflated and the catheter is removed from the patient's body.

While the invention has been described in connection with what is presently considered to be the most practical and preferred embodiments, it is to be understood that the invention is not to be limited to the disclosed embodiments but rather is intended to cover various modifications and equivalent arrangements included within the spirit and scope of the appended claims.

What is claimed, is:

1. An endovascular stent for resisting restenosis in a stenosed region of a blood vessel that has been expanded by balloon angioplasty, said stent comprising: a stent sleeve having an expandable tubular body portion containing a cross-linkable substance at least a portion of which can be cured by exposure to radiation, and a film of material which is biologically compatible with the vessel and encapsulating such tubular body portion to thereby isolate it from the vessel.

2. A stent as defined in claim 1 wherein said cross-linkable substance is selected from the group consisting of epoxys and urethanes.

3. A stent as defined in claim 2 wherein said cross-linkable substance is a polyurethane oligomer mixture.

4. A stent as defined in claim 3, wherein said encapsulating film of material is impregnated with an antithrombogenic agent.

5. A stent as defined in claim 2, wherein said encapsulating film is constructed of an elastic substance that remains integral during expansion of said tubular body portion.

6. A stent as defined in claim 1 wherein such tubular body portion contains a plurality of longitudinally disposed filaments composed of a noble metal.

7. A stent as defined in claim 6 wherein said elastic substance is a medical grade of silicone.

8. A stent as defined in claim 1 wherein said encapsulating film is constructed of an elastic substance that remains integral during expansion of said tubular body portion.

9. A stent as defined in claim 1 wherein said encapsulating film of material is impregnated with an antithrombogenic agent.

10. A stent as defined in claim 1 wherein said stent sleeve comprises a plurality of separate pockets that extend substantially parallel with respect to each other along said tubular body portion.

* * * * *